United States Patent
Goto

(10) Patent No.: US 8,206,402 B2
(45) Date of Patent: Jun. 26, 2012

(54) INCISION TOOL

(75) Inventor: Hiroaki Goto, Tokyo (JP)

(73) Assignee: Olympus Medical Systems Corp., Tokyo (JP)

( * ) Notice: Subject to any disclaimer, the term of this patent is extended or adjusted under 35 U.S.C. 154(b) by 947 days.

(21) Appl. No.: 12/117,401

(22) Filed: May 8, 2008

(65) Prior Publication Data

US 2008/0300594 A1    Dec. 4, 2008

(30) Foreign Application Priority Data

May 31, 2007  (JP) .................................. 2007-144874

(51) Int. Cl.
*A61B 17/24* (2006.01)
*A61B 18/18* (2006.01)

(52) U.S. Cl. ............................. 606/113; 606/46; 606/47

(58) Field of Classification Search .................. 606/170, 606/172, 32, 37–42, 45–50, 113; 600/566–567
See application file for complete search history.

(56) References Cited

U.S. PATENT DOCUMENTS

| | | | |
|---|---|---|---|
| 3,910,279 A | 10/1975 | Okada et al. | |
| 4,921,484 A | 5/1990 | Hillstead | |
| 6,471,697 B1 * | 10/2002 | Lesh | 606/41 |
| 7,585,298 B2 * | 9/2009 | Kawahara et al. | 606/45 |
| 2002/0029052 A1 | 3/2002 | Evans et al. | |
| 2004/0092953 A1 | 5/2004 | Salameh et al. | |
| 2004/0122457 A1 | 6/2004 | Weber | |
| 2005/0107664 A1 * | 5/2005 | Kalloo et al. | 600/115 |
| 2005/0148818 A1 * | 7/2005 | Mesallum | 600/116 |
| 2007/0088354 A1 * | 4/2007 | Sugita | 606/46 |
| 2010/0106151 A1 * | 4/2010 | Longo et al. | 606/33 |

FOREIGN PATENT DOCUMENTS

| | | |
|---|---|---|
| JP | S61-259662 A | 11/1986 |
| JP | S62-194847 A | 8/1987 |
| JP | H05-15918 | 3/1993 |
| JP | 8-509854 | 10/1996 |
| JP | 2000-237202 A | 9/2000 |
| JP | 2000-262539 A | 9/2000 |
| JP | 2004-073582 | 3/2004 |
| WO | WO 94/26013 | 11/1994 |
| WO | WO 00/51683 | 9/2000 |
| WO | WO 01/28445 A1 | 4/2001 |
| WO | WO 2004/041329 A2 | 5/2004 |

OTHER PUBLICATIONS

Extended European Search Report dated Mar. 3, 2010. Japanese Office Action dated Feb. 21, 2012 from corresponding Japanese Patent Application No. JP 2007-144874 together with an English language translation.

* cited by examiner

*Primary Examiner* — Linda C Dvorak
*Assistant Examiner* — Brian M Antiskay
(74) *Attorney, Agent, or Firm* — Scully, Scott, Presser & Murphy, PC

(57) ABSTRACT

An incision tool includes a sheath; a plurality of wires that are inserted through an internal space of the sheath, and that, as a result of a portion thereof being inserted through both first wire insertion through holes that are provided in a distal end portion of the sheath and second wire insertion through holes that are provided on the sheath distal end side of the first wire insertion through holes, are exposed on the outside of the sheath between the first wire insertion through holes and the second wire insertion through holes, and that receive high-frequency current; and an operating unit that is connected to a base end side of the wires and that adjusts the length of the exposed portions of the wires which are exposed on the outside of the sheath by moving forwards or backwards relatively to the sheath in the longitudinal direction of the wires.

4 Claims, 8 Drawing Sheets

INCISION TOOL

BACKGROUND OF THE INVENTION

1. Field of the Invention

The present invention relates to an incision tool that is used when a narrowing portion developed in an esophagus is incised.

Priority is claimed on Japanese Patent Application No. 2007-144874, filed May 31, 2007, the contents of which are incorporated herein by reference.

2. Description of Related Art

Conventionally, a method in which a balloon is used is known as a method of treating a narrowing portion developed in an esophagus. However, a treatment method which uses a balloon has the drawback that it is necessary in a large number of cases to perform repeated enlargement operations over a period of several weeks resulting in a lengthy period of treatment.

Because of this, a treatment method that uses an incision tool (see Japanese Utility Model Application No. 5-15918) to incise a narrowing portion of an esophagus by exposing wires on an outer side of a sheath, and then supplying high-frequency current to these wires has been proposed as one method of performing early treatment on an esophageal narrowing portion.

However, the following problems remain in the incision tool which is used in the aforementioned treatment method and which is disclosed in the aforementioned Japanese Utility Model Application No. 5-15918.

That is, in this incision tool, as a precondition, an operating unit that is manipulated by an operator is operated so that the wires that are connected to the operating unit are pushed out towards their distal end side, resulting in the exposed portion of the wires which are exposed on the outside of the sheath expanding outwards. However, at this time, conventionally, the distal end sides of the wires which should have stopped inside the sheath end up shifting towards the distal end side of the sheath. Because of this, it becomes impossible to farther expand the exposed wire portions to a desired shape, and consequently, the problem arises that a narrowing portion cannot be incised satisfactorily.

SUMMARY OF THE INVENTION

The incision tool of the present invention includes: a sheath; a plurality of wires that are inserted through an internal space of the sheath, and that, as a result of a portion thereof being inserted through both first wire insertion through holes that are provided in a distal end portion of the sheath and second wire insertion through holes that are provided on the sheath distal end side of the first wire insertion through holes, are exposed on the outside of the sheath between the first wire insertion through holes and the second wire insertion through holes, and that receive high-frequency current; and an operating unit that is connected to a base end side of the wires and that adjusts the length of the exposed portions of the wires which are exposed on the outside of the sheath by moving forwards or backwards relatively to the sheath in the longitudinal direction of the wires, wherein the plurality of wires each have a base end side insertion portion that is inserted into the internal space of the sheath on the base end side of the first wire insertion through hole, an exposed portion that extends from the base end side insertion portion towards the distal end side and passes through the first wire insertion through hole so as to be exposed on the outside of the sheath, a distal end side insertion portion that extends from the exposed portion towards the distal end side and passes through the second wire insertion through hole so as to enter again into the internal space of the sheath, and a bent portion that is provided in an end portion on the exposed portion side of the distal end side insertion portion and that bends the wire in the axial direction of the sheath from the direction in which it enters into the internal space of the sheath via the second wire insertion through hole, and wherein the plurality of wires are bound together into a single bundle in the distal end side insertion portion on the distal end side of the bent portions by a binding component.

In the incision tool of the present invention, it is also possible for an anchor portion whose diameter is larger than the diameter of the sheath to be provided in the sheath on the distal end side of the exposed portions of the wires.

In the incision tool of the present invention, it is also possible for the exposed portions of the plurality of wires that are exposed to the outside of the sheath between the first wire insertion through hole and the second wire insertion through hole to be arranged in a radial pattern around the center axis of the sheath.

In the incision tool of the present invention, it is also possible for a gradation scale that forms an index for adjustment of the length of the exposed portions of the wires to be formed on the operating unit.

DETAILED DESCRIPTION OF THE INVENTION

An embodiment of the present invention will now be described with reference made to the drawings.

Figure 2:
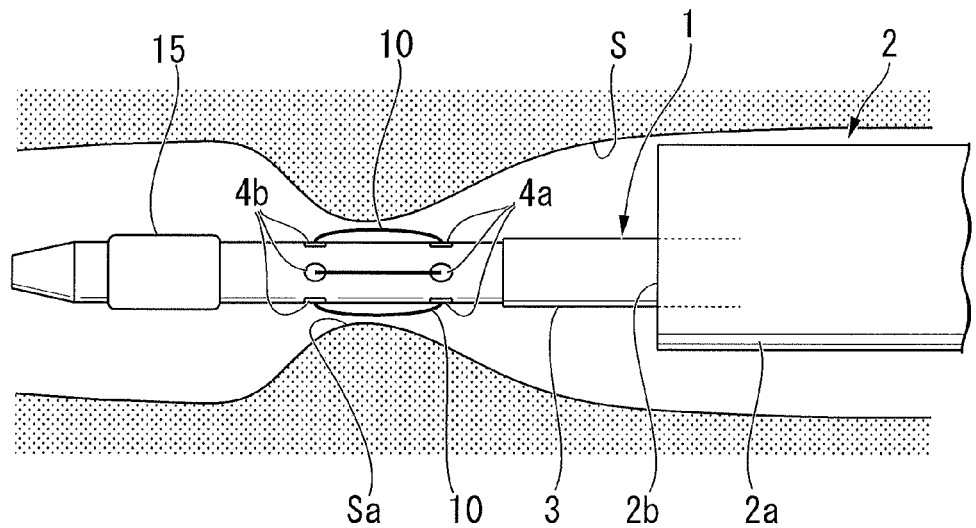
FIG. 2 is a cross-sectional view showing a distal end of this endoscope.
Figure 3:
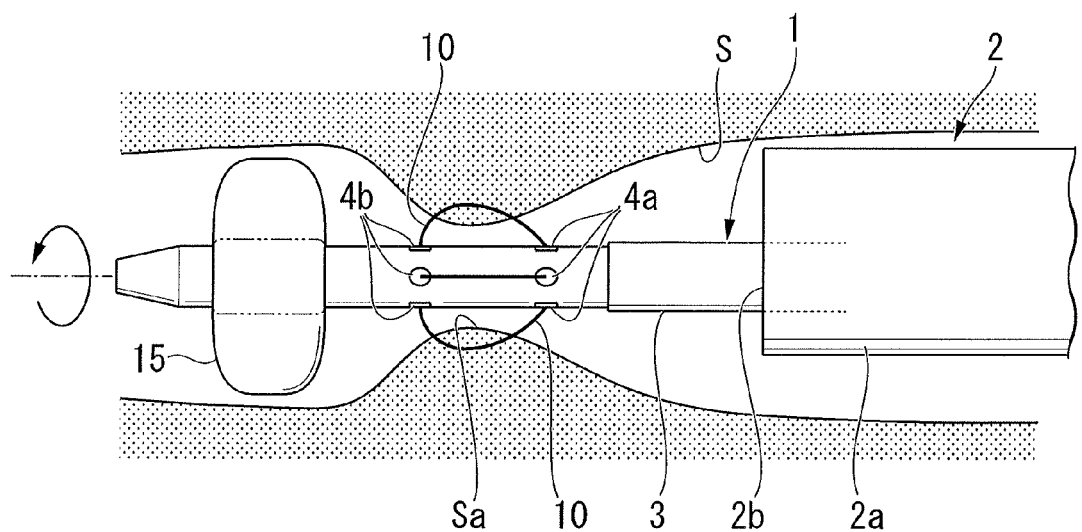
FIG. 3 is a cross-sectional view showing a state in which a narrowing portion of an esophagus is incised by this incision tool.

FIGS. 1 to 14 show an embodiment of an incision tool according to the present invention. In these drawings, FIG. 1 is a perspective view showing a state in which an incision tool is fitted into an endoscope, FIG. 2 is a cross-sectional view illustrating a state when an incision tool is inserted into an esophagus, and FIG. 3 is a cross-sectional view illustrating a situation in which a narrowing portion of an esophagus is incised by the incision tool.

Figure 1:
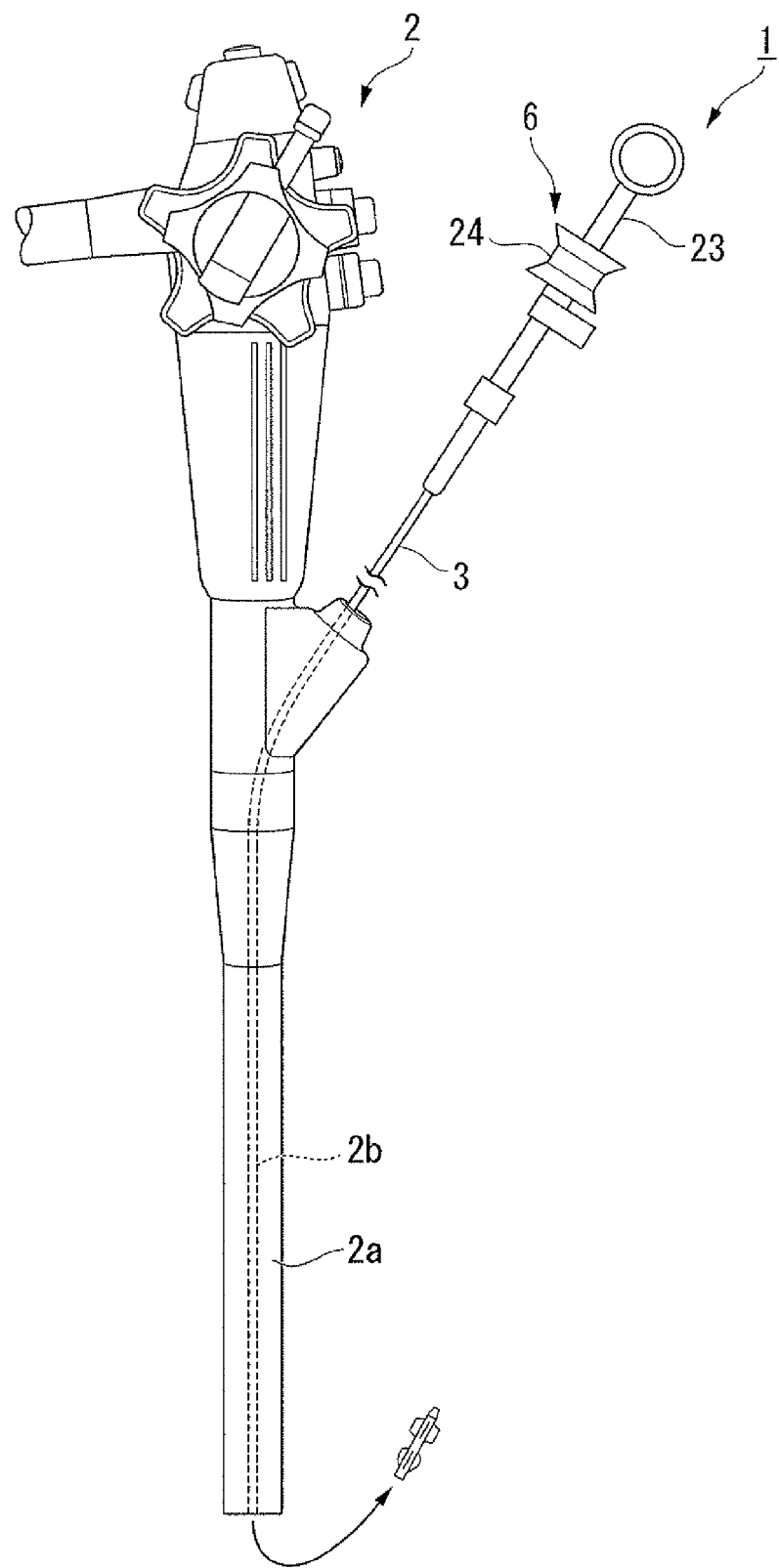
FIG. 1 is a perspective view showing a state in which an incision tool according to an embodiment of the present invention is fitted onto an endoscope.

As is shown in FIG. 1, an incision tool 1 of the present embodiment is used by being incorporated into an endoscope 2. As is shown in FIGS. 1 and 2, the incision tool 1 is provided with: a flexible sheath 3 that is formed by, for example, a coil sheath which has an internal insertion through hole 3a extending along its axis and that has sufficient flexibility to allow it to be inserted into a treatment tool channel 2b which is formed in an insertion portion 2a of the endoscope 2; a plurality of wires 5 that are inserted through the interior of the flexible sheath 3 and that form wire exposed portions 10 which are exposed on the outside of the flexible sheath 3 as a result of a portion thereof being inserted through first wire insertion through holes 4a that are provided in a distal end portion of the flexible sheath and through second wire insertion through holes 4b that are provided on the distal end side of the flexible sheath of the first wire insertion through holes 4a; and an operating unit 6 that is connected to one end side (i.e., a base end side) of the wires 5 and that adjusts the length of the exposed portions 10 of the wires which are exposed on the outside of the flexible sheath by moving forwards or backwards relatively to the flexible sheath 3 in the longitudinal direction of the wires 5.

Note that, here, the side of the incision tool 1 where the operating unit 6 is located is referred to as the base end side, while the opposite side therefrom is referred to as the distal end side.

Here, a first wire insertion through hole 4a and a second wire insertion through hole 4b that are formed in the flexible sheath 3 and through which the plurality of wires 5 are respectively inserted is formed for each one of the wires 5. That is, the same number of first wire insertion through holes 4a and second wire insertion through holes 4b are formed as the number of wires 5. Here, the first wire insertion through holes 4a are formed at the same position in the longitudinal direction of the flexible sheath 3, and the second wire insertion through holes 4b are also formed at the same position in the longitudinal direction of the flexible sheath 3. Moreover, these first and second wire insertion through holes 4a and 4b are formed at equidistant intervals in the circumferential direction.

Figure 4:
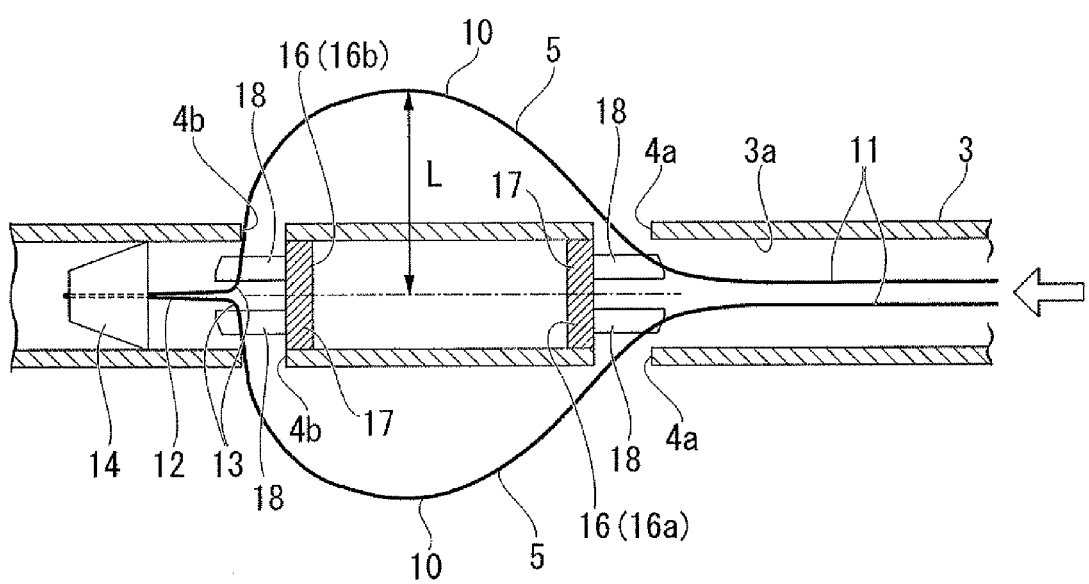
FIG. 4 is a cross-sectional view showing an internal portion of a flexible sheath at a distal end of this incision tool.
Figure 5A:
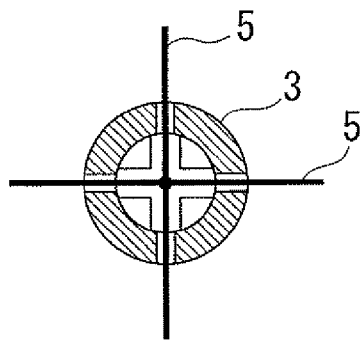
FIGS. 5A to 5D are front views showing examples of the layout of exposed wire portions of this incision tool.
Figure 5B:
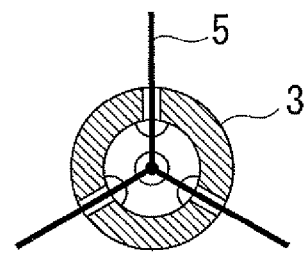
Figure 5C:
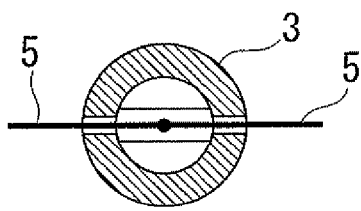
Figure 5D:
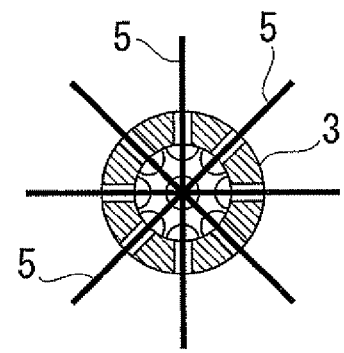
Figure 5E:
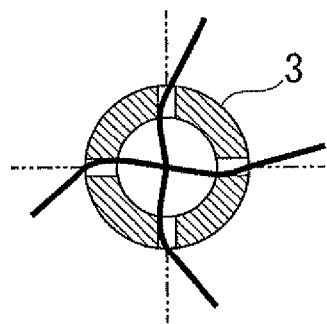
FIG. 5E is a front view showing a reference example of an exposed wire portion illustrated to provide a comparison for the present invention.

As is shown in FIG. 4, the plurality of wires 5 each have a base end side insertion portion 11 that is inserted into the internal space of the flexible sheath 3 on the base end side of the first wire insertion through hole 4a, the exposed portion 10 that extends from the base end side insertion portion 11 towards the distal end side and passes through the first wire insertion through hole 4a so as to be exposed on the outside of the flexible sheath 3, a distal end side insertion portion 12 that extends from the exposed portion 10 towards the distal end side and passes through the second wire insertion through hole 4b so as to enter again into the internal space of the flexible sheath 3, and a bent portion 13 that is provided in an end portion on the exposed portion 10 side of the distal end side insertion portion 12 and that bends the wire 5 in the axial direction of the flexible sheath 3 from the direction in which it enters into the internal space of the flexible sheath 3 via the second wire insertion through hole 4b. Moreover, the plurality of wires 5 are bound together into a single bundle by a binding component 14 on the distal end side of the bent portions 13.

The wires 5 are flexible and, as is shown in FIG. 2 and FIG. 3, when the operating unit 6 is moved forwards or backwards in the longitudinal direction of the wires, the shape of the exposed portions 10 is deformed so as to expand towards the outer side or to contract towards the inner side. Moreover, the wires 5 are conductive so that, when they are supplied with a high-frequency current, they function as a knife portion in which the exposed portions 10 incise biological tissue (specifically, an inner esophageal wall).

The wires 5 are inserted through a hole in the center of the binding component 14, and the placement of the wires 5 in the binding component 14 is fixed by frictional force generated by the elasticity of the binding component itself or by an adhesive agent or the like.

The binding component 14 is formed in a tapered shape which narrows towards its distal end side from a material having suitable elasticity and heat resistance. The maximum outer diameter of the binding component 14 is set to a slightly larger value than that of the inner diameter of the flexible sheath 3. As a result, the binding component 14 is engaged by a suitable frictional force with the inner surface of the flexible sheath 3.

A balloon 15 that can be inflated to a larger diameter than that of the flexible sheath 3 is mounted on the distal end side of the flexible sheath 3 beyond the exposed portions 10 of the wires. The balloon 15 is connected to an air supply via an air tube (not shown) that is located within the flexible sheath. When air is supplied into the balloon 15 through this air tube, then, as is shown in FIG. 3, the balloon is inflated outwards.

As is shown in FIGS. 5A through 5D, the number of wires 5 may be 4, 3, 2, or 8, or any plural number other than these. However, as is shown in these drawings, the exposed portions 10 of the wires are placed at equidistant angular intervals in the circumferential direction so as to radiate outwards.

Heat resistant coating processing is performed on the vicinity of the first wire insertion through holes 4a and the second wire insertion through holes 4b of the wires 5. As a result, heat from the wires 5 does not get directly transmitted to stabilizers 16 (described below).

As is shown in FIG. 4, stabilizers (i.e., wire restricting portions) 16 that restrict movement of the wires 5 such that the wires 5 extend in a normal direction relative to the outer surface of the flexible sheath 3 without twisting to the left or right, in other words, such that they do not diverge from the radial direction of the flexible sheath 3 when the exposed portions 10 of the wires 5 are expanded are provided in the vicinity of first and second wire insertion through holes 4a and 4b inside the flexible sheath 3.

Various types of stabilizers can be considered. For example, in the stabilizers shown in FIG. 4, stabilizers 16a and 16b that correspond to the first and second wire insertion through holes 4a and 4b both have the same configuration, and are placed on the inside of the flexible sheath 3 so as to be mutually symmetrical. They are fixed in position by a suitable fixing device such as an adhesive agent or by press-insertion or the like.

The stabilizer 16a on the base end side which corresponds to the first wire insertion through holes 4a is formed by a circular plate portion 17, and by four protruding portions 18 having a fan-shaped cross section that extend from one side of the circular plate portion 17 in a direction which is perpendicular to the circular plate portion 17. These protruding portions 18 are fixed in position so as to face towards the base end side. The stabilizer 16b on the distal end side which corresponds to the second wire insertion through holes 4b is also formed by a circular plate portion 17, and by four protruding portions 18 having a fan-shaped cross section that extend from one side of the circular plate portion 17 in a direction which is perpendicular to the circular plate portion 17. In the stabilizer 16b, the protruding portions 18 are fixed in position so as to face towards the distal end side.

Wire guide grooves are formed respectively between each protruding portion 18. The stabilizers 16a and 16b are fixed in position inside the flexible sheath 3 such that these wire guide grooves have the same angular position as each other in the stabilizer 16a on the base end side and the stabilizer 16b on the distal end side, and also such that the wire guide grooves each match the first and second wire insertion through holes 4a and 4b. The diameter of the wire guide grooves is set as a slightly larger value than that of the diameter of the wires 5.

Note that the stabilizers 16a and 16b are manufactured from a material having a suitable rigidity such as, for example, metal or hard plastic.

Figure 6A:
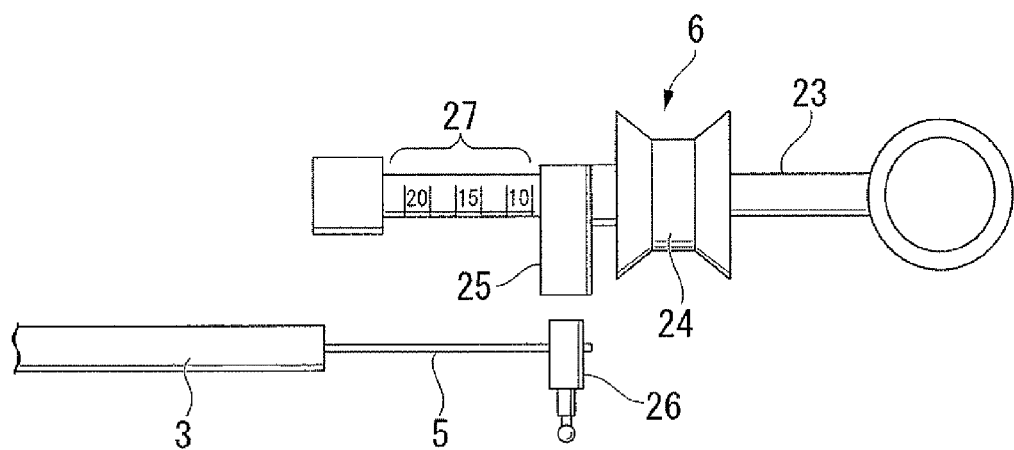
FIG. 6A is an exploded side view of an operating portion used in this incision tool.
Figure 6B:
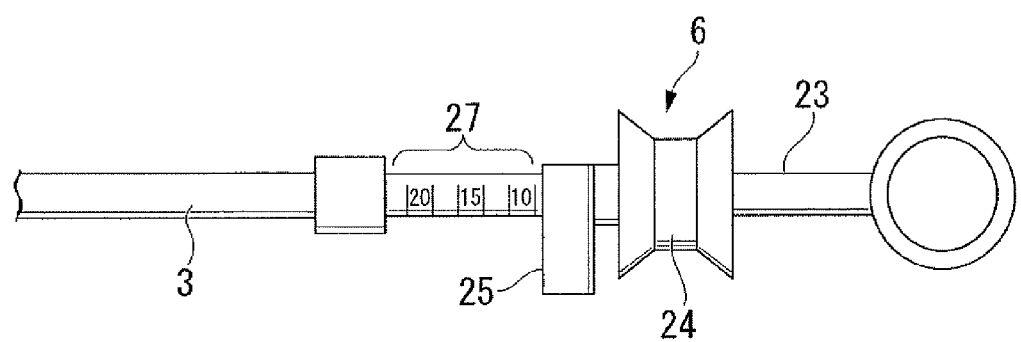
FIG. 6B is a side view of an operating portion used in this incision tool.

FIG. 6A is an exploded view of the operating unit, while FIG. 6B is a side view of the operating unit. As is shown in these drawings, a base end side of the flexible sheath 3 is connected to an operating unit main body 23. Guide grooves (not shown) are formed extending in the axial direction in an intermediate portion of the operating unit man body 23. A sliding portion 24 that slides along the guide grooves is fitted onto the operating unit main body 23. A terminal supporting portion 25 is provided integrally with the sliding portion 24 and an electrode terminal 26 is mounted on this terminal supporting portion 25. A base end of the wire 5 is connected to the electrode terminal 26, and a connection terminal (not shown) that extends from a high-frequency power supply is able to be connected to the electrode terminal 26.

A gradation scale (i.e., index) 27 is formed on the operating unit main body 23. The distance moved by the sliding portion 24 and, consequently, a rough guide of a clearance L between the exposed portions 10 of the wires and the axis of the flexible sheath are displayed by means of this gradation scale 27 (see FIG. 4).

Here, if the sliding portion 24 is moved forwards or backwards in the longitudinal direction of the wires 5, the base end sides of the wires 5 that are connected to the electrode terminal 26 that moves integrally with the sliding portion 24 move in the same direction, so that the movement of the wires is transmitted sequentially to the distal end side. As a result, as is shown in FIG. 4, the length of the exposed portion 10 of the wires is adjusted. That is, the operating unit main body 23 and the sliding portion 24 form the operating unit 6 which adjusts the length of the exposed portions 10 of the wires by moving the wires 5 forwards or backwards.

Next, an operation to incise a narrowing portion of an esophagus using an incision tool having the above described structure will be described.

Firstly, as is shown in FIG. 2, the exposed portions 10 of the wires are placed in a state of maximum contraction, and the balloon 15 is left in a deflated state. Next, the insertion portion 2a of the endoscope 2 is perorally inserted and guided into the interior of an esophagus S until a narrowing portion Sa is confirmed by means of endoscopic images. Once the location of the narrowing portion Sa has been confirmed, the flexible sheath 3 is inserted into the treatment tool channel 2b of the endoscope 2 as is shown in FIG. 1. The flexible sheath 3 is then made to protrude from the distal end of the insertion portion 2 while this operation is being confirmed by means of endoscopic images.

Next, as is shown in FIG. 2, the exposed portions 10 of the wires are moved opposite the narrowing portion S of the esophagus while the operation is being viewed using endoscopic images. Adjustments to the movement of the exposed portions 10 of the wires to a position opposite the narrowing portion S of the esophagus are made by adjusting the insertion amount of the insertion portion 2a of the endoscope 2 while the interrelationship between the endoscope and the incision tool is kept the same. Alternatively, it is also possible to leave the insertion state of the insertion portion 2a of the endoscope unchanged, and adjust the amount of protrusion of the flexible sheath 3 from the distal end of the insertion portion 2a.

After the exposed portions 10 of the wires have been moved opposite the narrowing portion Sa of the esophagus in this manner, as is shown in FIG. 3, the sliding portion 24 of the operating unit 6 is moved forwards in the longitudinal direction of the wires, so that the exposed portion 10 of each wire is expanded outwards. At the same time as this, air is supplied via an air tube (not shown) to inflate the balloon 15.

Here, when the sliding portion 24 is moved forwards in the longitudinal direction of the wire, the base end sides of the wires 5 which are connected to the sliding portion 24 move in the same direction, so that this movement of the wires 5 is sequentially transmitted to the distal end side. As a result, the distal end sides of the wires 5 receive force moving them forwards. At this time, the bent portions 13 are provided on the wire distal end side insertion portions 12, so that the transmitted force of the wire movement is divided by the bent portions 13. That is, on the distal end side of the wires, the bent portions 13 function as stoppers so that forward movement of the wires on the forward side of the bent portions 13 is restricted. In addition, in this embodiment, forward movement of the wires on the forward side of the bent portions 13 is also restricted by the binding component 14 which is provided as an auxiliary component. As a result, movement of the base end side of the wires 5 relative to the flexible sheath 3 is concentrated in the exposed portions 10 of the wires that are exposed to the outside of the flexible sheath 3 so that, as is shown in FIG. 3, the exposed portions 10 of the wires expand to the desired shape.

Here, the operation to expand the exposed portions 10 of the wires using the operating unit 6 and the operation to inflate the balloon 15 can be linked together and performed simultaneously.

For example, it is also possible to employ a structure in which, when the sliding portion 24 of the operating unit 6 is moved forwards, this movement of the sliding portion 24 is detected by a sensor and, based on this detection result, an air supply device (not shown) is operated so that a predetermined quantity of air is supplied to the balloon 15 inflating the balloon 15.

Moreover, stabilizers 16 are provided in the vicinity of the first wire insertion through holes 4a and the second wire insertion through holes 4b in the flexible sheath 3, and the exposed portions 10 of the wires 5 are guided by the wire guide grooves 19 in the stabilizers 16. Because of this, when the exposed portions 10 of the wires 5 expand, as is shown in FIGS. 5A through 5D, the exposed portions 10 of the wires 5 expand such that they extend in a normal direction relative to the outer surface of the flexible sheath 3. Accordingly, the exposed portions 10 of the wires 5 can be prevented from being twisted to the left or right as they expand in the manner shown in FIG. 5E, and they expand so as to radiate outwards while remaining positioned at equidistant angles in the circumferential direction. As is described below, this state is maintained in the same way while the incision tool 1 is being rotated and the narrowing portion Sa in the esophagus is being incised.

When the exposed portions 10 of the wires have expanded to the desired shape, the clearance L between the exposed portions 10 of the wires and the flexible sheath axis can be accurately ascertained based on the gradation scale 27 formed on the operating unit main body 23. Because of this, when the operating unit 6 is being operated, it is possible to prevent in advance the incision depth to which the exposed portions 10 of the wires incise the narrowing portion Sa of the esophagus becoming deeper than is necessary.

When the operating unit 6 is operated causing the exposed portions 10 of the respective wires to expand, this operation is performed while high-frequency current is supplied to the wires 5. Accordingly, when the exposed portions 10 of the wires are expanded, the incision is made to a predetermined position inside the narrowing portion Sa of the esophagus. Subsequently, the incision tool 1 is rotated together with the entire insertion portion 2a of the endoscope 2 while the high-frequency current is being supplied to the wires 5. This enables the narrowing portion Sa of the esophagus to be incised. Note that it is also possible for the incising of the narrowing portion Sa of the esophagus to be achieved by only rotating the incision tool 1 instead of rotating the entire insertion portion 2a of the endoscope.

At this time, because the balloon 15 has been inflated at a predetermined position on the distal end side of the exposed portions 10 of the wires, even if force is applied unintentionally in the extraction direction during the rotation, the inflated balloon 15 functions as an anchor portion so that the position of the incision tool 1 does not get shifted towards the base end side in the axial direction. That is, the exposed portions 10 of the wires are held in a position facing the narrowing portion Sa of the esophagus.

Moreover, as is described above, because the balloon 15 has been inflated at a predetermined position on the distal end side of the exposed portions 10 of the wires so that the distal end portion of the flexible sheath 3 is held in a substantially concentric position inside the esophagus by the balloon 15, it is possible to prevent the distal end portion of the flexible sheath which includes the exposed portions 11 of the wires being unintentionally shaken when the incision tool is rotated. As a result, a smooth incision of the narrowing portion Sa of the esophagus can be performed by the exposed portions 10 of the wires.

After the incision, the balloon 15 is deflated and the exposed portions 10 of the wires are contracted by operating the operating unit 6. In this state, the distal end portion of the incision tool 1 is retracted entirely within the channel in the endoscope, and the incision tool 1 is extracted to the outside of the body together with the endoscope.

Figure 7:
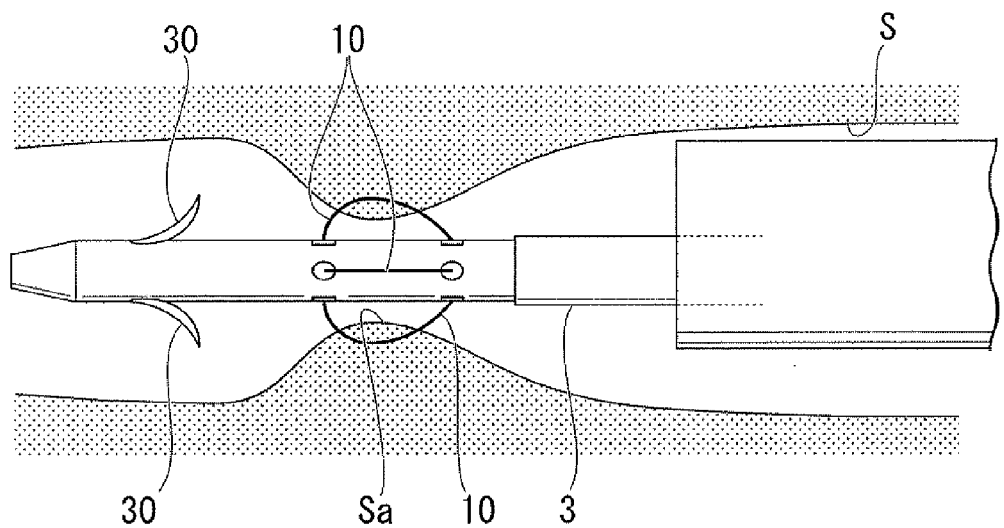
FIG. 7 is a cross-sectional view of a distal end portion showing a variant example of an incision tool according to embodiment of the present invention.

FIG. 7 shows a variant example of an embodiment of the present invention. In the above described embodiment, a balloon which is placed on the distal end side of the wire exposed portions 10 of the flexible sheath 3 is used as an anchoring portion in order to prevent the flexible sheath being pulled out after having been set in position and to prevent the distal end portion of the flexible sheath being shaken, however, here elastic flaps 30 are used instead of a balloon.

That is, just one end side of a plurality of elastic flaps 30 is fixed to the outer circumferential surface of the flexible sheath 3, and these elastic flaps 30 are shaped so as to expand gradually outwards moving towards the base end side of the flexible sheath.

These elastic flaps 30 have suitable elasticity so that when the distal end portion of the flexible sheath 3 is being inserted past a narrowing portion Sa of an esophagus, the elastic flaps 30 themselves are suitably deformed so as to allow the distal end portion of the flexible sheath 3 to move forwards. In contrast, after the incision tool has been set in a predetermined position, when force is applied in the direction in which the distal end portion of the flexible sheath is extracted, the free end portions of the elastic flaps 30 come up against the narrowing portion Sa of the esophagus. This prevents the incision tool 1 from coming loose. Moreover, when the flexible sheath 3 is being rotated, as a result of the distal end of the flexible sheath 3 coming into contact with the internal wall surface of the esophagus, it is possible to prevent any shaking of the distal end portion of the flexible sheath 3.

Note that in the example shown in FIG. 7, the number of elastic flaps 30 is set at three, however, the present embodiment is not limited to this and it is also possible for the number of elastic flaps 30 to be set at two or four or more.

Figure 8:
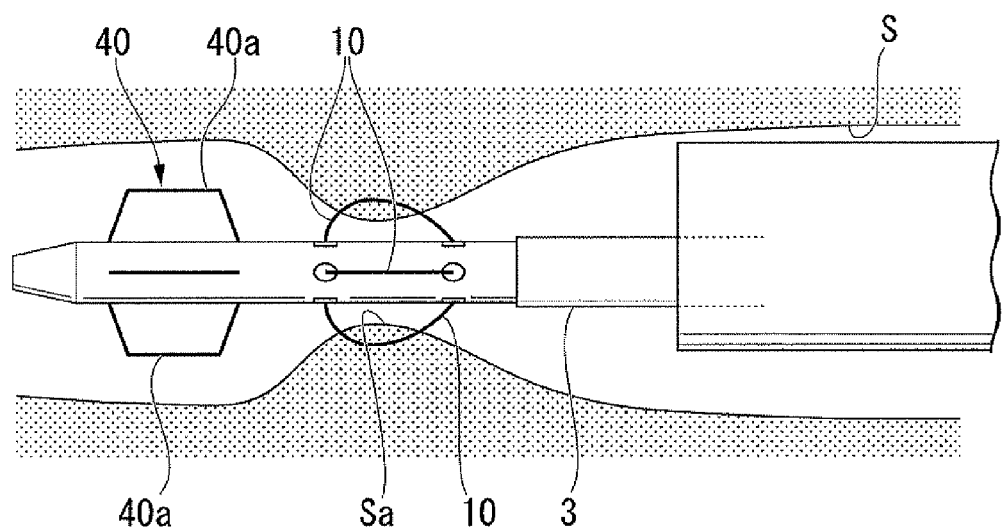
FIG. 8 is a cross-sectional view of a distal end portion showing another variant example of an incision tool according to embodiment of the present invention.

FIG. 8 shows another variant example of an embodiment of the present invention. Here, an expandable and contractible basket 40 is used as the anchor portion.

That is, here, the basket 40 is used as the anchor portion. When a plurality of deformable wire objects 40a that make up this basket 40 are made, for example, from metal, the wire objects 40a are connected individually or together in a single bundle while their insulation from the wires 5 is maintained to an operating unit (not shown) which expands or contracts the basket.

It is possible when this basket 40 is used as well, to achieve the function of preventing the flexible sheath being pulled out after it has been set in position and preventing the distal end portion of the flexible sheath being shaken.

Figure 9:
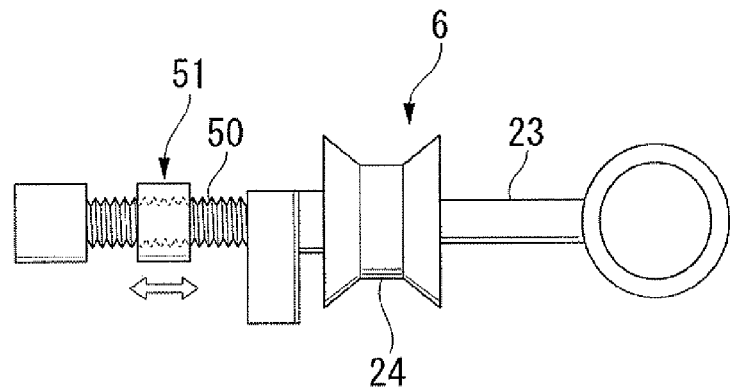
FIG. 9 is a side view of an operating portion showing another variant example of an incision tool according to embodiment of the present invention.

FIG. 9 shows a variant example of an embodiment of the present invention. In this example, a rotating ring 51 that screws onto a male threaded portion 50 that is formed on the operating unit main body 23 is used as a stopper to restrict movement of the sliding portion 24 towards the distal end side.

That is, by rotating the rotating ring 51, the rotating ring 51 can be moved in the longitudinal direction of the operating unit main body 23, and after the sliding portion 24 comes up against the rotating ring 51, any further movement thereof towards the distal end side of the flexible sheath is restricted by the moved rotating ring 51. As a result, when the operating unit 6 is being operated, it is possible to more reliably prevent the incision depth to which the narrowing portion Sa of the esophagus is incised by the exposed portions 10 of the wires becoming deeper than is necessary.

Figure 10A:
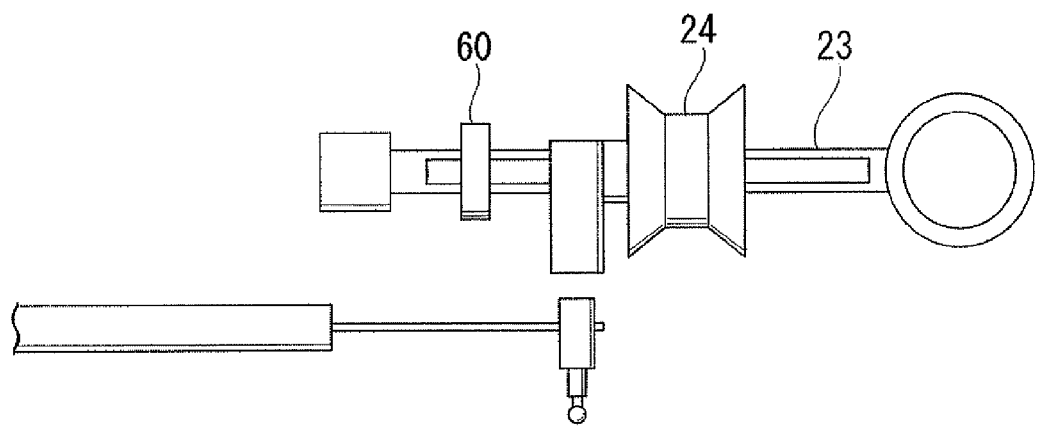
FIG. 10A is an exploded side view of an operating portion showing another variant example of an incision tool according to embodiment of the present invention.
Figure 10B:
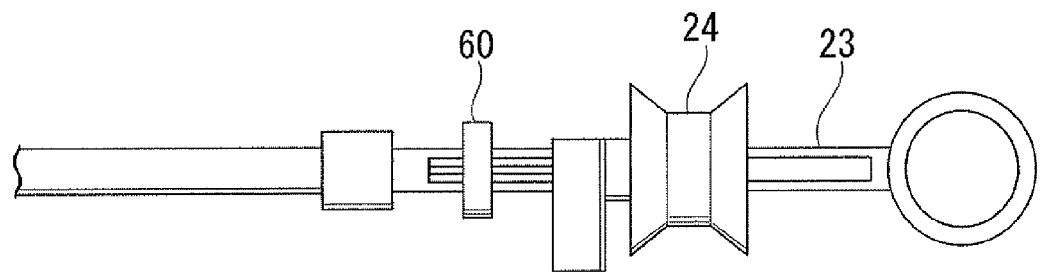
FIG. 10B is a side view of an operating portion showing a variant example of FIG. 10A.

FIGS. 10A and 10B show a variant example of an embodiment of the present invention. In this example, a stopper 60 is mounted directly on the operating unit main body 23, and after the sliding portion 24 comes up against the stopper 60, any further movement thereof towards the distal end side of the flexible sheath is restricted by the stopper 60.

The stopper 60 may be mounted on the operating unit main body 23 by being fixed thereon using an adhesive agent or the like, or it may be mounted on the operating unit main body 23 using friction such that it is able to move in the longitudinal direction of the operating unit main body 23.

Figure 11:
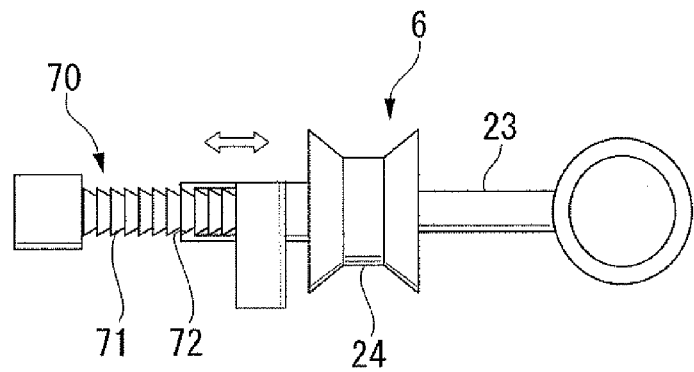
FIG. 11 is a side view of an operating portion showing another variant example of an incision tool according to embodiment of the present invention.

FIG. 11 shows a variant example of an embodiment of the present invention. In this example, a ratchet mechanism 70 is used between the sliding portion 24 and the operating unit main body 23 that make up the operating unit 6.

That is, an engaged portion 71 that is formed by a series of consecutive protruding portions and recessed portions extending in the circumferential direction is provided on the outer circumference of the operating unit man body 23, and an engaging claw 72 is provided on a distal end of an elastic arm that extends from the sliding portion 24. The flexible sheath distal end side of the distal end of the engaging claw 72 is orthogonal to the axis of the operating unit main body 23, while the flexible sheath base end side thereof is formed as a slope.

In this variant example, when the engaging claw 72 engages with the engaged portion 71, movement of the sliding portion 24 towards the distal end side of the flexible sheath progresses smoothly, however, conversely, movement of the sliding portion 24 towards the base end side of the flexible sheath is restricted by the ratchet mechanism 70. Accordingly, when the sliding portion 24 is moved towards the distal end side of the flexible sheath and the operation to expand the exposed portions of the wires which form a knife portion is performed in the step prior to the incision of a narrowing portion Sa of an esophagus, the ratchet mechanism 70 makes it possible to restrict movement of the sliding portion 24 back towards the base end side of the flexible sheath. It is therefore possible to keep the exposed portions 10 of the wires in an expanded state. Because of this, when the exposed portions of the wires are rotated either together with the entire endoscope or by rotating the incision tool alone in the step after the incision, an operator only needs to rotate the endoscope or the like in this state and does not have to apply force to the sliding portion 24, so that the incision operation is greatly simplified.

Figure 12A:
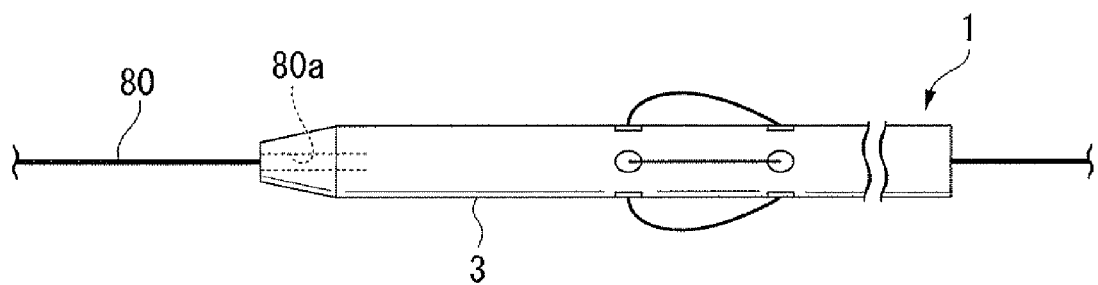
FIGS. 12A and 12B are both side views of a distal end portion showing yet another variant example of an incision tool according to embodiment of the present invention.
Figure 12B:
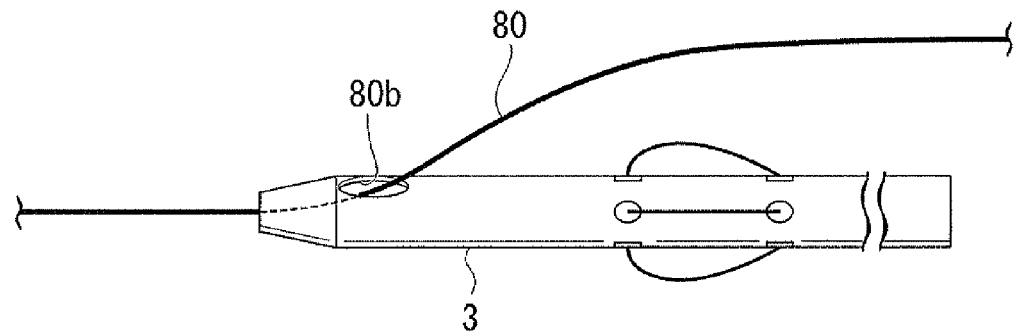

FIGS. 12A and 12B show another variant example of an embodiment of the present invention. In this example, when inserting the distal end of the incision tool 1 as far as a predetermined position of an esophagus so as to position it opposite a narrowing portion in the esophagus, a guide wire 80 is inserted beforehand into the esophagus and the distal end of the incision tool 1 is then inserted using this guide wire 80. The method used to engage the guide wire 80 with the incision tool 1 may be one in which, as is shown in FIG. 12A, the guide wire 80 is inserted through the complete length of an insertion through hole 80a which is formed inside the flexible sheath 3, or one in which, as is shown in FIG. 12B, the guide wire 80 is only inserted through a wire guide hole 80b which is formed in a distal end portion of the flexible sheath 3.

In either case, by using the guide wire 80 in this manner, the distal end of the flexible sheath 30 can be moved along the guide wire 80 so that it can safely transit the vicinity of a narrowing portion of an esophagus which is an extremely constricted position.

Note that the present invention is not limited to the above described embodiments and suitable design modifications may be made thereto insofar as they do not depart from the spirit or scope of the invention.

For example, in the above described embodiment, an anchor portion which is formed by the balloon 15 or the elastic flaps 30 or the like is provided on the distal end side of the exposed portion 10 of the wires which form a knife portion, however, this anchor portion is not an indispensable component in order for the present invention to be formed.

According to this incision tool, when the exposed portions of wires are positioned opposite a narrowing portion of an esophagus and, in this state, the operating unit is moved forwards in the longitudinal direction of the wires, the base end sides of the wires which are connected to the operating unit move in the same direction, so that this movement of the wires is sequentially transmitted to the distal end side. As a result, the distal end sides of the wires receive force moving them forwards. At this time, the bent portions are provided on the wire distal end side insertion portions, so that the transmitted force of the wire movement is divided by the bent portions. That is, on the distal end side of the wires, the bent portions function as stoppers so that forward movement of the wires on the forward side of the bent portions is restricted. As a result, movement of the wires relative to the sheath is concentrated in the exposed portions of the wires that are exposed to the outside of the sheath so that the exposed portions of the wires expand to the desired shape.

In this state, the narrowing portion of the esophagus is incised by supplying high frequency current to the wires and causing the incision tool to rotate around the sheath axis.

According to this incision tool, because the anchor portion is provided in the sheath on the distal end side of the exposed portions of the wires, the incision tool can be prevented by this anchor portion from shifting towards the base end side in the axial direction of the sheath. Because of this, it is possible to incise the required location with a high degree of stability. Moreover, when the incision tool is being rotated so that it cuts a narrowing portion of an esophagus, the anchor portion comes up against the internal wall of the esophagus which makes it possible to prevent any shaking of the distal end of the sheath and enables the incision to be made smoothly.

According to this incision tool, the length of the exposed portions of the wires and, consequently, the clearance between the exposed portions of the wires and the axis of the sheath, That is, the depth to which the biological tissue is incised can be accurately ascertained by observing the gradation scale on the operating unit. Accordingly, it is possible to prevent in advance the incision amount becoming deeper than is necessary.

According to this incision tool, when the incision tool is being rotated so that it cuts a narrowing portion of an esophagus, the narrowing portion is incised uniformly at equidistant angles, thereby enabling the incision to proceed smoothly.

According to the present invention, by moving an operating unit forwards, it is possible to expand exposed portions of wires to a desired shape, and consequently make a superior incision in a narrowing portion.

While preferred embodiments of the invention have been described and illustrated above, it should be understood that these are exemplary of the invention and are not to be considered as limiting. Additions, omissions, substitutions, and other modifications can be made without departing from the spirit or scope of the present invention. Accordingly, the invention is not to be considered as limited by the foregoing description and is only limited by the scope of the appended claims.

What is claimed is:

1. An incision tool comprising:
   a sheath;
   a plurality of wires that are inserted through an internal space of the sheath, and that, as a result of a portion thereof being inserted through both first wire insertion through holes that are provided in a distal end portion of the sheath and second wire insertion through holes that are provided on a sheath distal end side of the first wire insertion through holes, are exposed on an outside of the sheath between the first wire insertion through holes and the second wire insertion through holes, and that receive high-frequency current;
   an operating unit that is connected to a base end side of the wires and that adjusts a length of the exposed portions of the wires which are exposed on the outside of the sheath by moving forwards or backwards relatively to the sheath in a longitudinal direction of the wires; and
   wire restricting portions that are formed in a position corresponding to the first wire insertion through holes and the second wire insertion through holes, wherein the wire restricting portions comprise a circular plate portion that is formed in a direction which is perpendicular to an axial direction of the sheath, and comprises protruding portions that extend from one side of the circular plate portion in a direction which is perpendicular to the circular plate portion;

the protruding portions comprise wire guide grooves that extend to the axial direction of the sheath;

the plurality of wires each have a base end side insertion portion that is inserted into the internal space of the sheath on the base end side of the first wire insertion through hole, an exposed portion that extends from the base end side insertion portion towards the distal end side and passes through the first wire insertion through hole so as to be exposed on the outside of the sheath by being guided by the wire guide grooves, a distal end side insertion portion that extends from the exposed portion towards the distal end side and passes through the second wire insertion through hole so as to enter again into the internal space of the sheath by being guided by the wire guide grooves, and a bent portion that is provided in an end portion on the exposed portion side of the distal end side insertion portion and that bends the wire in the axial direction of the sheath from the direction in which it enters into the internal space of the sheath via the second wire insertion through hole, and wherein the plurality of wires are bound together into a single bundle in the distal end side insertion portion on the distal end side of the bent portions by a binding component.

2. The incision tool according to claim 1, wherein an anchor portion whose diameter is larger than a diameter of the sheath is provided in the sheath on the distal end side of the exposed portions of the wires.

3. The incision tool according to claim 1, wherein the exposed portions of the plurality of wires that are exposed to the outside of the sheath between the first wire insertion through hole and the second wire insertion through hole are arranged in a radial pattern around a center axis of the sheath.

4. The incision tool according to claim 1, wherein a gradation scale that forms an index for adjustment of the length of the exposed portions of the wires is formed on the operating unit.

* * * * *